United States Patent [19]

Kaelble

[11] 4,119,610

[45] Oct. 10, 1978

[54] BROMINATED ACRYLATE DENTAL COMPOSITIONS

[75] Inventor: David H. Kaelble, Thousand Oaks, Calif.

[73] Assignee: Arroyo Dental Products Co., La Canada, Calif.

[21] Appl. No.: 790,487

[22] Filed: Apr. 25, 1977

[51] Int. Cl.² ............................................. C08F 20/22
[52] U.S. Cl. .......................................... 526/292; 32/1; 204/159.23; 427/2; 427/140; 526/242; 560/221; 560/209
[58] Field of Search ................... 204/159.23; 526/242, 526/292; 260/47 UA

[56] References Cited

U.S. PATENT DOCUMENTS

| | | | |
|---|---|---|---|
| 3,515,656 | 6/1970 | Huang et al. | 526/292 |
| 3,607,847 | 9/1971 | Troussier et al. | 526/292 |
| 3,770,811 | 11/1973 | Lee et al. | 526/292 |

*Primary Examiner*—Harry Wong, Jr.
*Attorney, Agent, or Firm*—Marvin E. Jacobs

[57] ABSTRACT

Dental restorative, pit and fissure sealant compositions having improved environmental resistance include a brominated acrylate such as dibromopropyl methacrylate and/or a diacrylate of the formula:

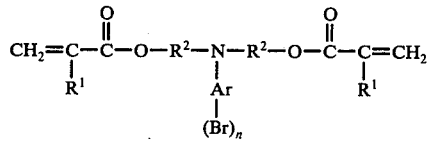

where $n$ is an integer from 1 to 6, $R^1$ is hydrogen or alkyl of 1 to 6 carbon atoms, $R^2$ is alkylene of 1 to 5 carbon atoms or

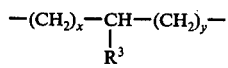

where $R^3$ is hydrogen, alkyl of 1 to 4 carbon atoms or —OH and $x$ and $y$ are selected from 0 or an integer from 1 to 4 and Ar is a cyclic group, preferably an aromatic group.

10 Claims, 2 Drawing Figures

BROMINATED ACRYLATE DENTAL COMPOSITIONS

BACKGROUND OF THE INVENTION

1. Field of the Invention

The present invention relates to novel brominated diacrylates, the synthesis thereof and to various thermosetting dental restorative compositions including the diacrylates.

2. Description of the Prior Art

Thermosetting diacrylates have been widely used in various fileds such as electrical potting-compounds and especially as dental restorative materials. The most widely used binder for the dental materials in BIS-GMA which is the adduct of two moles of methacrylic acid and the diglycidyl ether of Bisphenol A. Composite materials including finely divided fillers such as treated silica or quartz are disclosed in U.S. Pat. Nos. 3,066,112 and 3,835,090. Many such compositions are commercially available and have proved to be very useful in dental restorative applications.

Though the curing properties and compressive strength properties are satisfactory, the flow, wetting and adhesive properties on untreated, etched and hydrophobic treated enamel are not satisfactory especially in the humid saliva environment. The available diacrylate compositions do not perform satisfactorily in the sealing of small pits or fissures.

SUMMARY OF THE INVENTION

Novel diacrylates are provided in accordance with the invention which have more optimum surface energy characteristics and better water resistance for an environmentally resistant dental fissure sealant, an adhesive or a composite material. The novel diacrylates better approach optimum properties in terms of high dispersion and low polar components of surface tension. The novel diacrylates cure similarly to, are compatible with and can be formulated with presently utilized acrylate components of dental compositions. Both moisture uptake and extractable moisture are lower than BIS-GMA. Thermochemical analysis (TMA) of cured films show higher rigidity than BIS-GMA films.

The diacrylates of the invention are symmetrical compounds having a central brominated aryl amine nucleus providing hydrophobicity and desirable polar properties. The diacrylates are selected from compounds of the formula:

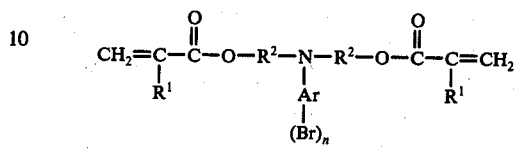

where $n$ is an integer from 1 to 6, $R^1$ is hydrogen or alkyl of 1 to 6 carbon atoms, $R^2$ is alkylene of 1 to 5 carbon atoms or

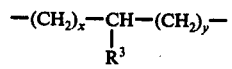

where $R^3$ is hydrogen, alkyl of 1 to 4 carbon atoms or —OH and $x$ and $y$ are selected from 0 or an integer from 1 to 4 and Ar is a cyclic group, preferably an aromatic group.

The aryl group may be monocyclic such as phenyl, polycyclic such as biphenyl, condensed ring compounds such as anthracenyl, aralkylene such as diphenyl methane or diphenylethane or heterocyclic such as pyrolle. Ar can also be a cycloaliphatic group containing 4 to 10 carbon atoms such as cyclohexyl, cyclooctyl and the like.

The diacrylates can be synthesized by reaction of an acylic acid with a diglycidyl compound as follows:

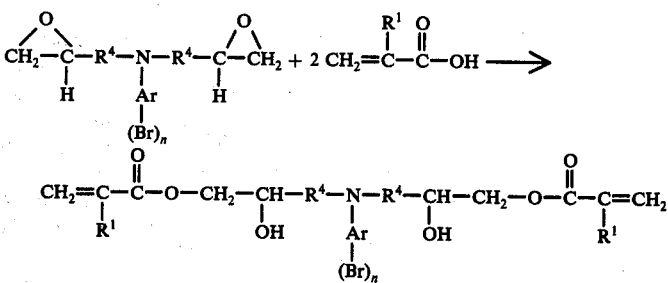

where $R^4$ is alkylene of 1 to 4 carbon atoms or by reaction of a cyclic diol with a glycidyl methacrylate as follows:

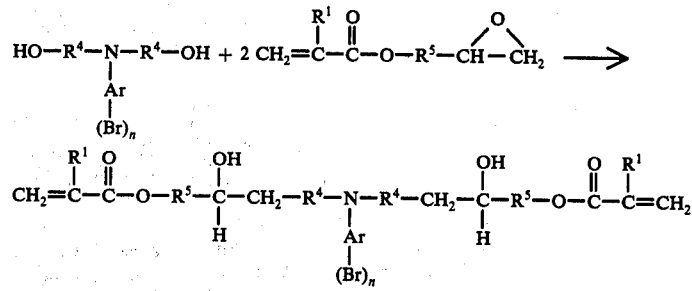

where $R^5$ is alkylene of 1 to 4 carbon atoms.

These and many other features and attendant advantages of the invention will become readily apparent as the invention becomes better understood by reference to the following detailed description when considered in conjunction with the accompanying drawings.

DESCRIPTION OF THE PREFERRED EMBODIMENTS

Figure 1:
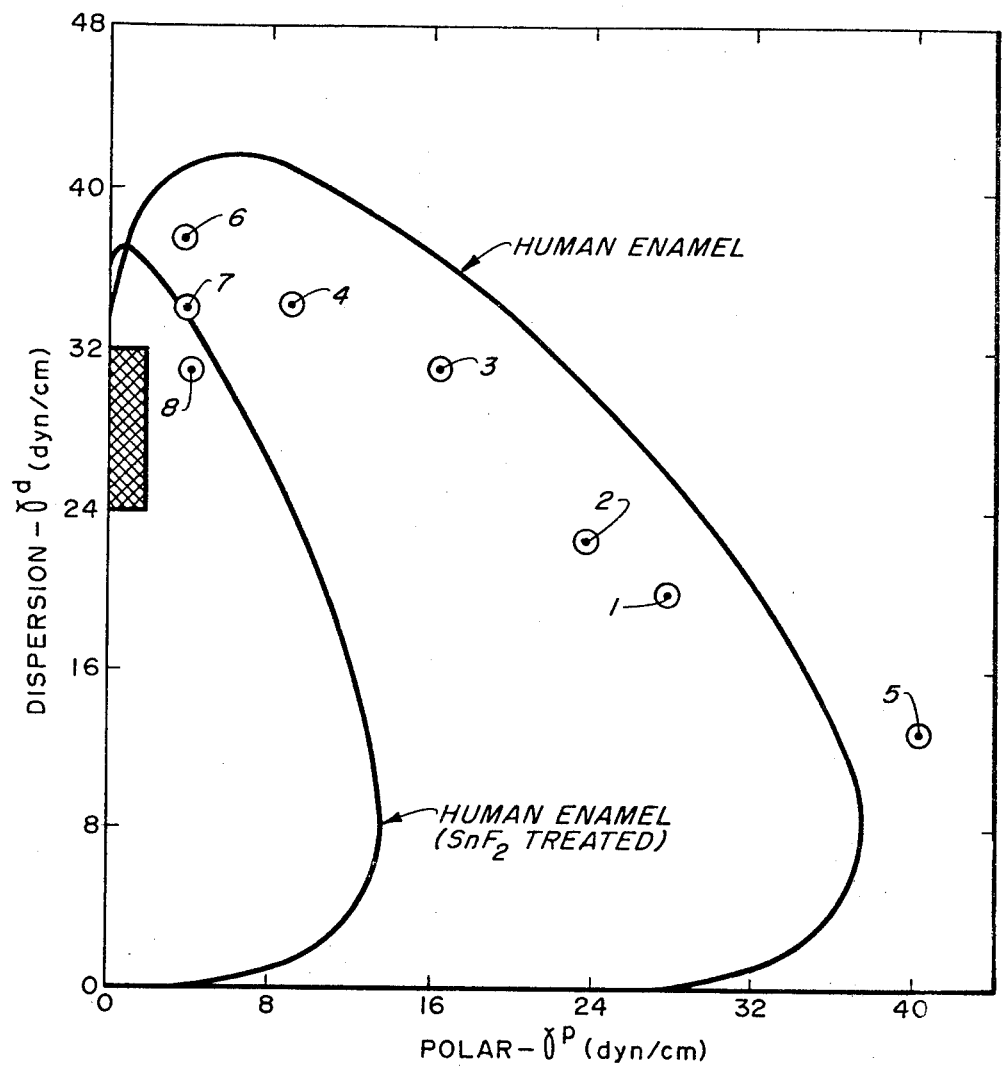
FIG. 1 is a Surface Energy Diagram showing wettability envelopes for Human Enamel (curves) and $\gamma^d$, $\gamma^p$ values (circles) for dental cements or sealants.

Idealized criteria for a dental sealant has been determined by means of considering the dispersion and polar characteristics of the diacrylates in relation to human enamel and to hydrophobic stannous fluoride treated enamel. Referring now to FIG. 1, polished human enamel displays solid surface tension properties $\gamma_{sv}^d = 30.7 \pm 5.0$ dyn/cm and $\gamma_{sv}^p = 23.3 \pm 6.6$ dyn/cm typifies the most wettable of tooth surfaces. Stannous fluoride ($SnF_2$) treated human enamel displays $\gamma_{sv}^d = 36.5 \pm 1.9$ dyn/cm and $\gamma_{sv}^p = 1.3 \pm 0.4$ dyn/cm typifies the least wettable of tooth surfaces. These differing ranges of wettability are shown in FIG. 1 by the wettability envelope curves. The area between the respective curve and the origin $\gamma^d = \gamma^p = 0$ defines a condition of complete spreading of liquids on the solid surface defined by the wettability envelope. Outside the respective envelope liquids are predicted to be nonwetting and fail to spontaneously displace air from the tooth surface. The farther a potential bonding agent, defined by $\gamma^d$, $\gamma^p$ points on FIG. 1, lies outside the wettability envelope the poorer is the predicted bonding. The farther a point lies inside the envelope the better the spreading and wetting. The preferred range is shown in the shaded area of FIG. 1.

Table 1 summarizes the surface tension values of commericial dental restorative compositions, a composition of the invention (A), a composition (B) of companion application entitled DENTAL RESTORATIVE AND PIT AND FISSURE SEALANT COMPOSITIONS, filed concurrently herewith, Ag-amalgam, 5, and polymethylmethacrylate, 6, as reference points.

$\sigma_c$, and related adhesive bond strength, varies with $R/R_o$ and that $\sigma_c = 0$ when $R = R_o$.

According to Kaelble (J. Appl. Polymer Sci. 18:1869, 1974) the failure criteria for propogation of a crack at an interface is:

$$\sigma_c = \left[ \frac{E_1 E_3}{\phi_1 E_3 + \phi_3 E_1} \frac{2(R^2 - R_o^2)}{\pi C} \right]^{\frac{1}{2}} \geq 0$$

where $E_1$, $E_3$ are the Young's moduli of the two materials; the fractional lengths are defined as $$\phi_1 = 1 - \phi_3 = L_1/(L_1 + L_3)$$

and $$R^2 = (\alpha_2 - \frac{1}{2}(\alpha_1 + \alpha_3))^2 + (\beta_2^2 - \frac{1}{2}(\beta_1 + \beta_3))^2$$

$$R_o^2 = \frac{1}{4}[(\alpha_1 - \alpha_3)^2 + (\beta_1 - \beta_3)^2]$$

A consequence of this equation is that if in an immersion phase $R \leq R_o$, $\sigma_c = 0$ and failure occurs in the absence of an external load. This is the case often observed when sealants are placed on smooth, moist enamel surfaces; without the mechanical bonding produced by acid etching, debonding occurs at virtually zero load. In order to maximize the stress needed to induce fracture between an adhesive and enamel, it is necessary to maximize R and minimize $R_o$.

To predict the durability of a resin-enamel bond in the oral cavity the surface tension properties of saliva must be known. Initially, calculations were based on the assumption that saliva and water were similar in surface tension properties. Preliminary measurements by Arroyo and several previous studies indicate that stimulated whole saliva has a somewhat lower total surface tension than pure water. Glantz in the latest investigation measured both the total surface tension $\gamma_{LV}$ and the dispersion component $\gamma_{LV}^d$ of saliva. These studies indicate that saliva has about a 20 dyn/cm lower surface tension than water, and Glantz's work shows this to be due mainly to reduction of the polar surface component $\gamma_{LV}^p$.

This theory can be graphically illustrated by plotting $\alpha = (\gamma^d)^{\frac{1}{2}}$ vs. $\beta = (\gamma^p)^{\frac{1}{2}}$. A hypothetical sealant placed

TABLE I

| Composition | Cure | Point on Figure 1 | Surface Energetics dyn/cm | | |
|---|---|---|---|---|---|
| | | | $\gamma_{sv}^D$ | $\gamma_{sv}^P$ | $\gamma_{sv}$ |
| Epoxylite 9075 | Ambient | 1 | 20.3 ± 3.5 | 27.5 ± 4.3 | 47.8 ± 1.0 |
| Delton | Ambient | 2 | 22.6 ± 3.3 | 23.7 ± 4.5 | 46.3 ± 2.0 |
| BIS GMA | Ambient | 3 | 31.2 ± 3.8 | 16.3 ± 3.6 | 38.6 ± 1.5 |
| Compound B | Thermal | 7 | 30.2 ± 2.1 | 4.4 ± 1.0 | 34.4 ± 1.3 |
| Compound B | U.V. Cure | 8 | 34.8 ± 2.5 | 3.8 ± 1.0 | 38.6 ± 1.5 |
| Compound A | Ambient | 4 | 34.8 ± 3.1 | 8.9 ± 2.0 | 43.7 ± 1.4 |
| Ag-Amalgam | | 5 | 13.2 ± 0.8 | 40.2 ± 0.9 | 53.4 ± 0.11 |
| PMMA | | 6 | 37.3 ± 2.1 | 3.5 ± 0.8 | 40.8 ± 1.3 |

As shown in FIG. 1 all dental adhesives except Ag-amalgam lie within the wettability envelope for human enamel. Alternatively all surface tension values except those for Compound B are shown to lie outside the wettability envelope for $SnF_2$ treated human enamel. However Compound A is far superior to the commercial materials and has low polar energy component.

Figure 2:
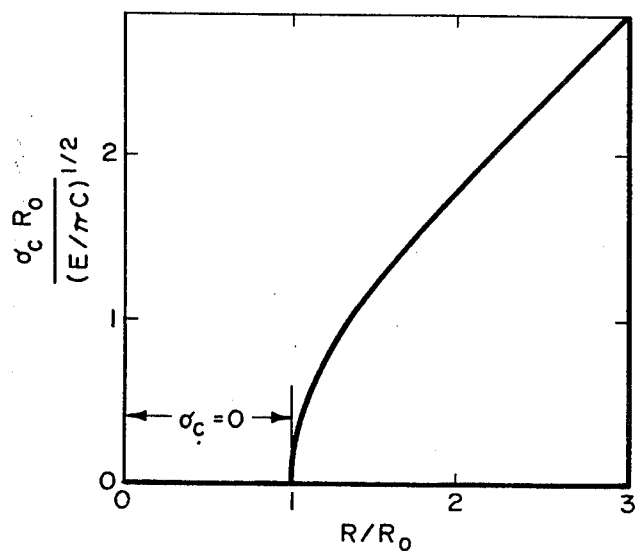
FIG. 2 is a graphical depiction of modified Griffith crack propogation theory.

A recent extension of surface energy analysis now treats the fractional degree of degradation in the critical stress $\sigma_c$, required to initiate a Griffith crack propogation at a bonded interface. This theory is graphically developed in FIG. 2 and shows that the critical stress on a treated enamel surface will have the surface energy characteristics located on the diagram. The two points located by the sealant and the enamel locate a circle; the radius of this circle is $R_o$ in the above formula. The values for $R_{water, air\ and\ saliva}$ are also identified. In effect, as long as R is greater than $R_o$, a finite stress is required to propogate a fracture at the interface. Highest resistance to fracture will occur when R is as long as possible and $R_o$ is very small. Since the oral environment contains air, water, saliva and other phases, it is necessary to consider R for each phase with respect to $R_o$. A resin designed to bond well to enamel in the presence of air may fail in the presence of saliva. If R for a given environment becomes equal to or less than $R_o$, failure occurs at zero load. In the case of a hydrophobic resin bonded to a hydrophilic enamel surface, such as an acid etched surface, discounting the effects of mechanical bonding, $R_{water} = R_o$, water penetrates between the resin and enamel, breaking any chemical bonding. A similar problem occurs with $SnF_2$ treated enamel surfaces. It is recognized that sealants have poor retention to $SnF_2$ treated surfaces because of reduced acid etching. In addition, because $R_{saliva}$ falls very close to $R_o$, the stress needed to cause interfacial fracture is very small or zero. This circumstance is observed clinically.

Griffith failure analysis of commercial sealants predicts the interface response for Epoxylite 9075 sealant (Table I). This bond presents a large R(air) vector for immersion in air with $\alpha_2 = \alpha_2 = 0$. Conversely, immersion in water with $\alpha_2 = 4.67$ and $\beta_2 = 7.14$ produces a small $R(H_2O)$ vector and a prediction of substantial reduction in crack propogation stress. However, the interface response predicted for Compound A (Table 1) on stannous fluoride ($SnF_2$) treated human enamel, presents a low polar characteristic so that R(air) is substantially equal to $R(H_2O)$ with the prediction of equal interfacial bond strength in air and water. The analysis thus projects a new result in that a nonpolar (low $\beta$) sealant bonded to a tooth specifically surface treated to be nonpolar (low $\beta$) should produce a moisture insensitive bonded interface.

Compound A is the methacrylic ester of N,N-diglycidyl tribromoaniline and has the following formula:

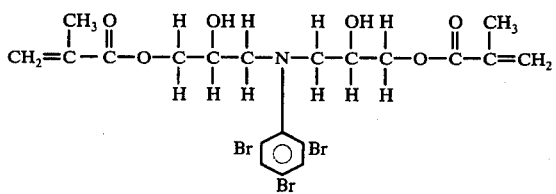

Resins based on Compound A show substantial promise in providing a bond to enamel with improved environmental resistance since the surface energetics more closely fit those of enamel surfaces. This minimizes $R_o$ and reduces the zone of debonding. Since Compound A is compatible with BIS-GMA and with compound B it can be copolymerized with Compound B and/or BIS-GMA to provide a polymer having surface energetics very closely fitting those of tooth enamel surfaces.

Compound A was synthesized as follows:

EXAMPLE 1

Preparation of the N,N Dichlorohydrin of Tribromoaniline 400 grams (1.21 moles) of tribromoaniline; 928.4 grams (10.0 moles) of epichlorohydrin; and 128.48 grams (2.14 moles) of glacial acetic acid are mixed in a 2 liter-3 necked flask equipped with a trubore stirrer, reflux condenser, and a nitrogen gas inlet tube. The flask is heated with an oil bath controlled by a variac. The reaction is heated to a bath temperature of 110° C. while a nitrogen blanket is maintained for 20 hours.

The flask containing the reaction mixture is equipped with a downward condenser, Perkin Triangle, receiving flask, and nitrogen bubbler. The first vacuum is 25 mm. The flask is stirred and heated to a temperature of 100° C. (oil bath). During this time the majority of the excess reagents distill over. At this point the pressure is further reduced to 1.0 mm. and the balance of the distillable reactants are removed at 100° C. bath temperature.

EXAMPLE 2

Conversion of N,N Dichlorohydrin of Tribromoaniline to the N,N Diglycidyl Derivative 496 grams, out of a total of 974 grams of the previously prepared chlorohydrin, is dissolved in 1175 ml. methyl ethyl ketone at reflux in a 4 liter resin kettle equipped with a stirrer and reflux condenser.

203.8 grams (5.09 moles) of sodium hydroxide brought to a total volume of 855 ml. with deionized water is added over ½ hour.

The mixture is then heated and stirred for an additional 2 hours. At this time the reaction mixture is cooled to room temperature and the mixture is separated into organic and aqueous phases. The organic layer is washed three times with deionized water until the pH of the aqueous layer is 7.0. At this point the organic phase is heavier than water. It is separated and placed in a stoppered Erlenmeyer flask and dried with CP anhydrous magnesium sulfate overnight.

The methyl ethyl ketone solution of the N,N diglycidyl tribromaniline is filtered free of the magnesium sulfate dessicant. It is placed in a 2 liter-3 necked flask equipped with nitrogen sparge tube, trubore stirrer, downward condenser, and receiver.

The pressure is reduced to 25 mm. and the flask is heated with an oil bath to 100° C. The bulk of the solvent is removed in this manner. Finally the pressure is reduced to 1.0 mm. and the remaining solvent is removed.

An optional method of removing the last traces of the ketone is the use of the rotary evaporator under 1.0 mm pressure.

The resulting red-brown oil is then ready for the crystallization procedure. This involves the seeding of the oil with true crystals of the diglycidyl compound. The oil is placed in a refrigerator and allowed to crystallize over a period of days.

The crude crystals are separated from the oil, either by gravity filtration or vacuum filtration. The crude crystals have an oxirane value of 0.37 equiv/100 grams of compound. This corresponds to 84% purity with a yield of 47.7%.

The recrystallization of this material is accomplished by dissolving the crude product in methanol at 50° C. In order to obtain a very pure crystalline product a considerable loss of material is found to occur. The overall yield is in the region of 30%. The oxirane value of the pure compound is 0.45 equiv/100 grams of compound. Tables 2 and 3 compare the Infrared Spectra of a true sample of diglycidyl tribromoaniline and the best preparation from the present synthesis.

EXAMPLE 3

Preparation of the Adduct of Methacrylic Acid and N,N Diglycidyl Tribromoaniline 125.0 grams (0.38 moles) of diglycidyl tribromoaniline are placed in a 500 ml.-3 necked flask, equipped with a stirrer and reflux condenser.

31.15 grams (0.36 moles) of methacrylic acid; 0.156 grams dibutylsulfide; 0.156 grams tertiary butyl paracresol; and 3.123 grams stannous octoate catalyst are added. The reaction is heated at 60° C. oil bath temperature for 12 hours.

The product is a straw-colored viscous material with an initial density of 1.71 (20° C.), and a free methacrylic acid content of 25-35%.

Compositions containing the brominated acrylates according to the invention cure to a solid rigid condition by means of free radical initiation either by ultraviolet radiation or by the use of peroxides or other materials capable of generating free radicals. Ambient cure at room temperature, e.g. about 20° C. to 30° C. is readily effected by addition of a peroxide polymerization catalyst and an activator which functions to cause rapid decomposition of the peroxide to generate free radicals.

A variety of peroxide polymerization catalysts as known in the art can be used, benzoyl peroxide, 2-4-dichlorobenzoyl peroxide and 4-chlorobenzoyl peroxide being representative thereof. The catalyst is generally employed in amounts from 0.1 to 1.0% by weight based on the weight of active monomer or monomers present.

Similarly, an activator or accelerator material which causes decomposition of the catalyst is employed in the formulation, such as, for example, N,N-dialkylanilines and N,N-dialkyltoluidines, in which the alkyl is alkyl or hydroxyalkyl of 1 to 4 carbon atoms.

The activator is generally employed in amounts ranging from about 0.1 to 1.0 weight percent based on the weight of the monomer or monomers present.

Ultraviolet curing formulations generally include from 1 to 5%, usually 1.5 to 3% by weight of an ultraviolet sensitizer such as benzoin methyl ether (BME).

For convenience in use, the composite dental filling compositions can be formulated in a form adapted for ready mixing by the dentist or other user. Thus a first part can be formulated containing the resin-forming monomer, inorganic filler and activator while a second part can contain the monomer, filler and peroxide, approximately the same proportions of monomer and filler being present in each part for convenience, although not necessarily limited to such proportions. Upon mixing of the two parts, polymerization of the monomer or monomers is initiated with the working or hardening time being variable and controllable by use of more or less of the activator.

The brominated acrylates are generally blended with other compatible mono, di, or tri acrylates to adjust viscosity, curing properties, surface energy characteristics and physical properties. Any of the monomers used in previous dental sealants or composites may be blended with the acrylates of the invention up to the solubility limit thereof. Representative monomers are methyl methacrylate (MMA), triethylene glycol dimethacrylate (TEGDM), ethylene glycol dimethacrylate (EGDM), tetraethylene glycol dimethacrylate, 1,3-butylene glycol dimethacrylate, trimethylolpropane trimethacrylate, BIS-GMA and dimethacrylate esters of BIS-Fluoroalkyl-fluoralkyl compounds disclosed in our copending application, Ser. No. 790,488, entitled DENTAL RESTORATIVE AND PIT AND FISSURE SEALANT COMPOSITIONS, filed concurrently herewith, the disclosure of which is incorporated herein by reference. The brominated acrylate can also be a reactive diluent such as dibromopropyl methacrylate (DBPM) or dibromopropyl dimethacrylate.

Higher compressive strength products are provided by addition of from 50% to 80% by weight of a finely divided inorganic filler such as quartz, silica, alumina or silane treated quartz or silica. The refractive index of the filler should be matched to the binder resin. Four formulations were prepared containing 49% by weight of Compound A, 49% of DBPM, EGDM, TEGDM or MMA comonomer and 2% benzoin methyl ether (BME). All of the formulations cured readily under ultraviolet light initiation. The curing time can be adjusted by varying the amount of initiator (BME) placed in the resin or by adding accelerators or retarders to the formulation. The conventional materials used for these purposes are expected to be compatible with resin A.

Formulations 1 and 2 have viscosities similar to those of the commercial sealants. Formulation 3 is too viscous for use as a selant due to the high viscosity of the diluent (tetraethylene glycol dimethacrylate). This diluent is suitable for applications of resin A which require high viscosity such as a bracket adhesive. Formulation 4 has a viscosity significantly less than those of commercial sealants due to the very low viscosity of the diluent methyl methacrylate. This low viscosity could be very helpful in obtaining improved penetration into narrow fissures and pits.

The surface energy characteristics of these four formulations and for commercial sealants are presented in Table 2.

TABLE 2

| SURFACE ENERGIES OF PIT AND FISSURE SEALANT FORMULATIONS | | | |
|---|---|---|---|
| Composition | $\gamma SV \pm \delta$ dynes/cm | $\gamma^d SV \pm \delta^d$ dynes/cm | $\gamma^p SV \pm \delta^p$ dynes/cm |
| Resin A | 43.3 ± 1.6 | 28.8 ± 2.6 | 14.6 ± 3.2 |
| Formulation 1 A + DBPM | 39.5 ± 0.9 | 30.9 ± 1.9 | 8.6 ± |
| Formulation 2 A + EGDM | 44.5 ± 1.0 | 31.6 ± 2.8 | 12.9 ± 2.6 |
| Formulation 3 A + TEGDM | 45.8 ± 0.9 | 29.2 ± 3.3 | 16.7 ± 3.3 |
| Formulation 4 A + MMA | 44.2 ± 0.9 | 29.7 ± 3.2 | 14.5 ± 2.9 |
| BIS-GMA | 47.5 ± 1.3 | 31.2 ± 3.2 | 16.5 ± 3.6 |
| Lee 9075 | 47.8 ± 1.0 | 20.3 ± 3.5 | 27.5 ± 4.3 |
| J & J Delton | 46.3 ± 2.0 | 22.6 ± 3.3 | 23.7 ± 4.5 |
| Caulk Nuv-A-Seal | 47.6 ± 1.8 | 30.2 ± 2.9 | 17.4 ± 3.3 |

Formulation 1 has a high total surface energy similar to those of commerical sealants, and the surface energy is composed of a high dispersion energy component with low polar energy. This low polar energy component is substantially different in character from that for commercial sealants or pure BIS-GMA. Note that this mixture of resin A with DBPM as a diluent has lower polar energy than resin A alone; the diluent not only reduces the viscosity to a level similar to commercial sealants but also reduces the polar energy component of the total surface energy without loss of dispersion energy. This combination of characteristics should favor bonding to a hydrophobic enamel surface with substantially improved resistance to environmental attack.

In addition, the DBPM diluent is radiopaque to dental X-rays. This degree of radiopacity is not likely to be observable in pit and fissure sealant applications due to the small thickness of the material, but the radiopacity may be very helpful in other applications of resin A.

Formations 2, 3 and 4 have total surface energies similar to commercial sealants, high dispersion energies and intermediate polar energies. Note in Table 2 that these formulations have energy characteristics very similar to those of pure BIS-GMA, while formulation 2 has a viscosity similar to those commercial sealants (BIS-GMA diluted), and formulation 4 has a much lower viscosity than commercial sealants. These mixtures should provide working characteristics similar to or better than commercial sealants while having improved adhesive bond resistance to the environment.

The glass transition temperature of the cured resin represents the transition from liquid to solid responses in amorphous materials. In the case of a sealant, a glass transition temperature slightly above body temperature would provide a "tough" material more capable of withstanding repeated force applications then brittle, high Tg, polymers. Table 3 presents glass transition temperature data for the sealant formulations and commercial products.

TABLE 3
GLASS TRANSITION TEMPERATURES

| Composition | Tg Cured °C. |
|---|---|
| Resin A | 38 ± 25 |
| Formulation 1 A + DBPM | 67 ± 16 |
| Formulation 2 A + EDGM | 94 ± 13 |
| Formulation 3 A + TEGDM | 77 ± 10 |
| Formulation 4 A + MMA | No transition observed |
| BIS-GMA | 40 ± 20 |
| Lee 9075 | 37 ± 12 |
| J & J Delton | 53 ± 16 |

Note that resin A and BIS-GMA have Tg values slightly above body temperature, indicating this "toughness" characteristic. Adding the DBPM, EGDM or TEGDM diluents substantially increases the Tg, representing increased brittleness in the mixture.

Compound A cures readily using ultraviolet activation. Compound A is a liquid at 23° C. as required to achieve wetting and spreading on the tooth surface and curing achieves solidification by raising the liquid-glass transition temperature, Tg. Moisture uptake and extractables are lower in Compound A as compared to BIS-GMA. Thermomechanical analysis (TMA) of cured films of A show this material is nearly comparable to BIS-GMA in thermal response. Compound A is comparable in cure time with commercial sealants. Shear adhesion bond strength to unetched bovine enamel is higher for Compound A than BIS-GMA.

An ambient cure procedure follows:

EXAMPLE 4

One drop (0.05 ml) of activator is mixed with 1 gm of Compound A.

| Fast parts, gm | Activator | Slow parts, gm |
|---|---|---|
| 100 | TEGDM*(250 ppm MEHQ) | 100 |
| 15 | DMPT* | 5 |
| 0.5 | BHT* | 0.5 |

*TEGDM = Triethylene glycol dimethacrylate
*DMPT = N,N-dimethylpara toluidine
*BHT = Butylated hydroxy toluene
*MEHQ = Methyl ether of hydroquinone Halving the amount of DMPT produces one-fourth the reaction rate.

This mixture is stirred to provide complete mixing and entrained bubbles are removed by vacuum or standing. This mixture forms the activated dental resin.

Addition of one drop (0.05 ml) of the following initiator with mixing initiates cure which proceeds spontaneously at temperature from 23° C. to 37° C.

| Initiator | parts, gm |
|---|---|
| Methyl methacrylate | 25 |
| BHT | 0.2 |
| Dibenzoyl peroxide | 1.0 |

The glass transition temperature Tg measures the transition from liquid to solid state response in amorphous materials. The resin system must have Tg below 23° C. in order to display liquid properties for wetting and spreading. Conversely, the cured resin must display Tg above room temperature in order to display solid state properties to develop bond strength and freacture toughness.

The Tg of a material can be conveniently measured using a less than 50 mgm sample by DSC where the step increase in heat capacity $C_p$ from glass state $(C_p)_G$ to liquid state $(C_p)_L$ appears on the thermogram. The midpoint of this transition is taken as Tg and the transition bond width between glass and liquid state response is reported as a plus and minus on Tg. The sharpness of Tg is a measure of compound purity. The temperature difference $T-Tg>0$ has a large effect on viscosity.

A summary of Tg measurements by DSC using a scan rate of 20° C./min is presented in Table 4.

TABLE 4

| Example | Sample Wt (mgm) | Number of scans | Tg(° C) |
|---|---|---|---|
| A1 | 18.84 | 2 | −40 ± 8 |
| A2 | 18.01 | 3 | −21 ± 11 |
| A3 | 24.40 | 3 | − 2 ± 6 |
| A4 | 14.97 | 4 | − 8 ± 6 |
| A5 | 19.00 | 4 | − 6 ± 6 |
| A6 | 32.61 | 4 | − 8 ± 11 |
| B3 | 15.81 | 1 | −15 ± 8 |
| C1 | — | 4 | − 5 ± 8 |

One notes a progressive increase in Tg of samples A1 through A6 which appears to coincide with improvements in resin synthesis and purification to provide an average value of $Tg = -7° ± 6°$ C. as the midpoint and range for this uncured resin. Curing Compound A using the Example 4 formulation with ambient cure temperature produces a Tg change of $\Delta Tg = 45°$ C. and broadens the Tg range to $Tg = 38° ± 25°$ C. The broadened Tg range in the cured resin may be evidence of network imperfections in the cured system. Post curing this specimen for 1 hour at 177° C. increased the Tg by 20° C. indicating that further curing proceeds at a highly elevated temperature.

Tg characterization of Compound B shows a monomer $Tg = -15°$ C. which is about 10° C. lower than either Compound A or BIS-GMA. Curing Compound B by ambient temperature UV cure produces a Tg change of $\Delta Tg = 121°$ C. to provide a cured $Tg = 106° ± 10°$ C. Thermal curing of BP catalyzed Compound B at temperatures to 170° C. produces a closely equivalent Tg change of $\Delta Tg = 7°$ C. to a final value of $Tg = 132°$ C. BIS-GMA is similar to Compound A in both uncured and cured Tg values. Post curing for 1 hour at 177° C. raises Tg by $\Delta Tg = 7°$ C. to a final value of $Tg = 48°$ C.

It is evident that the Tg values of uncured Compounds A, B, and BIS-GMA are comparable. Curing Compound B produces a much larger change in Tg and presumably a more solid response character at ambient temperatures due to the high Tg. Post curing experiments show that Tg is further increased in Compounds A, B, and BIS-GMA suggesting that ambient cured materials possess network defects which react via cross-linking at elevated temperature where T>Tg (cured resin).

A summary of other test results follows:

TABLE 5

| | Moisture Uptake | |
|---|---|---|
| | Ambient, % $H_2O$ | 7 day, 37° C, % $H_2O$ |
| Example 4 | 0.00 | 2.81 |
| Compound B | 0.19 | 1.98 |
| BIS-GMA | 0.38 | 3.62 |
| | Moisture Extractables | |
| | 7 day, 37° C in $H_2O$ | |
| Example 4 | 1.33 | |
| Compound B | 0.00 | |
| BIS-GMA | 2.61 | |
| | Bond Strength - Shear adhesion to unetched Bovine Enamel | |
| | All Samples, lbs/in² | All non-zero samples, lbs/in² |
| Example 4 | 72.6 ± 58.8 | 87.1 ± 53.4 |
| BIS-GMA | 46.2 ± 66.2 | 69.1 ± 86.2 |

EXAMPLE 5

25 pbw of 2,3-dibromopropyl methacrylate (DBRM) were copolymerized under argon and ultraviolet with 100 pbw of Compound B containing 2 pbw BME and 10 pbw of MMA. The material set in 20 seconds and showed Dumbell tensile strength of 44 kg/cm² and a diametrical tensile strength of 82 kg/cm². The proportional limit was the same on the tensile strength.

This example demonstrates that the non-polar character of Compound B can be retained using DBPM as a diluent for bracket adhesive applications. Furthermore, copolymerization of BIS-GMA with 50% DBPM lowers the modulus temperature response to a level similar to Nuv-A-Seal.

The surface energy characterization of dental resins A, B, and BIS-GMA together with several copolymer formulations and commercial products has been completed and is presented in Table 6.

TABLE 6

| SURFACE ENERGY PROPERTIES | | | | | |
|---|---|---|---|---|---|
| | $\gamma_{sv}^d \pm \delta^d$ | $\gamma_{sv}^P \pm \delta^p$ | $\gamma_{sv} \pm \delta$ | $\alpha$ | $\beta$ |
| Compound A | 28.8±2.6 | 14.6±3.2 | 43.4±1.6 | 5.37 | 3.82 |
| Compound A | 29.3±2.3 | 15.2±2.6 | 44.5±1.3 | 5.41 | 3.90 |
| Compound B | 23.0±1.8 | 4.7±1.1 | 27.6±1.5 | 4.79 | 2.17 |
| Compound C (BIS-GMA) | 30.3±2.9 | 15.8±3.1 | 46.1±1.2 | 5.50 | 3.97 |
| Polyethylene glycol dimethacrylate (EGDM) | 28.3±2.5 | 17.6±3.0 | 45.9±1.2 | 5.32 | 4.19 |
| Poly 2,3 dibromopropyl methacrylate (DEPM) | 31.2±1.7 | 6.3±0.9 | 37.5±0.9 | 5.59 | 2.51 |
| Polytetraethylene glycol dimethacrylate (TEGDM) | 30.4±3.1 | 16.1±3.5 | 46.4±1.4 | 5.51 | 4.01 |
| 100pbw SC-A8 + 100pbw EGDM | 31.6±2.8 | 12.9±2.6 | 44.5±1.0 | 5.62 | 3.59 |
| 100pbw SC-A8 + 100pbw DBPM | 30.9±1.9 | 8.6±1.3 | 39.5±0.9 | 5.56 | 2.93 |
| 100pbw SC-A8 + 100pbw MMA | 29.7±3.2 | 14.5±2.9 | 44.2·.·0.9 | 5.45 | 3.81 |
| 100pbw SC-A8 + 100pbw TEGDM | 29.2±3.3 | 16.7±3.3 | 45.8±0.9 | 5.40 | 4.09 |
| 10pbw DBPM + 100pbw A | 27.7±1.9 | 13.3±2.0 | 40.9±0.9 | 5.26 | 3.65 |
| 25pbw DBPM + 100pbw A | 29.3±2.1 | 11.5±1.8 | 40.8±0.8 | 5.41 | 3.39 |
| 100pbw DBPM + 100pbw A | 32.4±1.7 | 6.4±1.0 | 38.8±0.9 | 5.69 | 2.53 |
| 25pbw DBPM + 100pbw B | 26.7±1.5 | 3.4±0.7 | 30.0±1.2 | 5.17 | 1.84 |
| Johnson & Johnson: DELTON | 29.5±3.2 | 16.5±3.2 | 46.0±1.0 | 5.43 | 4.06 |
| Caulk: NUVA-SEAL | 30.2±2.9 | 17.4±3.7 | 47.6±1.8 | 5.50 | 4.17 |
| Lee: EPOXYLITE 9075 | 29.0±3.3 | 16.7±3.3 | 45.8±0.8 | 5.39 | 4.09 |

As shown in Table 6 and as discussed earlier the low polar ($\gamma$ sv$^p$) surface energy properties necessary for an environmentally resistant fissure sealant can be obtained by copolymerization of Compound A with 2,3 dibromopropyl methacrylate (DBPM). It has also been found that the nonpolar character of Compound B can be retained using DBPM as a diluent for bracket adhesive applications.

An extensive study has been made of the surface energy of combinations of Compounds A with B and BIS-GMA is given in Table 7.

TABLE 7

| SURFACE ENERGY PROPERTIES OF COPOLYMERS OF RESINS A AND B | | | | |
|---|---|---|---|---|
| | $\gamma_{sv}^D \pm \delta d$ | $\gamma_{sv}^P \pm \delta p$ | $\gamma_{sv} \pm \delta$ | $\alpha$ | $\beta$ |
| | (dyn/cm) | | | (dyn/cm)$^{\frac{1}{2}}$ |
| | Cured under Argon | | | | |
| Pure Compound A | 29.3±2.3 | 15.2±2.6 | 44.5±1.3 | 5.41 | 3.90 |
| Pure Compound B | 23.0±1.8 | 4.7±1.1 | 27.6±1.5 | 4.79 | 2.17 |
| 1 pbw B in 1000 pbw A | 25.2±1.9 | 10.0±2.0 | 35.1±1.4 | 5.01 | 3.16 |
| *1 pbw B in 100 pbw A | 23.9±2.0 | 8.4±1.8 | 32.3±1.4 | 4.89 | 2.90 |
| 3 pbw B in 100 pbw A | 21.6±2.0 | 12.1±2.1 | 33.7±1.0 | 4.65 | 3.48 |
| 5 pbw B in 100 pbw A | 21.8±2.2 | 13.2±2.3 | 35.1±1.0 | 4.67 | 3.62 |
| 10 pbw B in 100 pbw A | 21.3±1.5 | 4.3±1.0 | 25.5±0.8 | 4.62 | 2.07 |
| 15 pbw B in 100 pbw A | 27.9±2.2 | 7.2±1.5 | 35.1±1.5 | 5.28 | 2.6 |
| 1 pbw A in 100 pbw B | 23.1±1.8 | 5.5±1.2 | 28.7±1.4 | 4.81 | 2.35 |
| *5 pbw A in 100 pbw B | 24.5±1.6 | 5.3±1.0 | 29.8±1.1 | 4.95 | 2.30 |

*solubility limit

It was found that the polar suface component of either BIS-GMA or Compound A could be reduced from 15-16 dyn/cm to 7-8 dyn/cm by addition of 1% Compound B. This composition is just below the solubility limit of B in A or BIS-GMA. The dispersion surface energy component was affected very little in these formulations. The addition of Compound B to Compound A beyond the solubility limit shows a more complicated behavior.

The solubility and surface energy of Compounds A and BIS-GMA in Compound B wal also studied. Compounds A and BIS-GMA show 5-10% solubility in Compound B but as shown in Table 7 the surface energy of B was not affected.

Mixtures of Compound A and BIS-GMA are miscible in all proportions and the nearly equal surface energy properties of these two resins was unchanged in the formulations studied, see Table 8 below.

TABLE 8
SURFACE ENERGY PROPERTIES OF COPOLYMERS OF RESINS A AND BIS-GMA (C)

| Composition | $\gamma_{sv}^d \pm \delta^d$ | $\gamma_{sv}^p \pm \delta^p$ | $\gamma_{sv} \pm \delta$ | $\alpha_c$ | $\beta_c$ |
|---|---|---|---|---|---|
| | (dyn/cm) | | | (dyn/cm)$^{\frac{1}{2}}$ | |
| Pure Compound A | 29.3±2.3 | 15.2±2.6 | 44.5±1.3 | 5.41 | 3.90 |
| Pure Compound C | 30.3±2.9 | 15.8±3.1 | 46.1±1.2 | 5.50 | 3.97 |
| 30 pbw A in 100 pbw C | 29.5±2.9 | 13.7±2.7 | 43.5±1.0 | 5.43 | 3.70 |
| 50 pbw A in 100 pbw C | 28.3±2.9 | 17.7±3.6 | 46.0±1.7 | 5.32 | 4.20 |

In summary these findings show that it is possible to reduce the hydrophilic surface properties of either Compound A or BIS-GMA by adding small amounts of B to these resins.

It is to be realized that only preferred embodiments of the invention have been described and that numerous substitutions, modifications and alterations are permissible without departing from the spirit and scope of the invention as defined in the following claims.

What is claimed is:

1. An ambient curing composition comprising a solution of a brominated diacrylate compound selected from compounds of the formula:

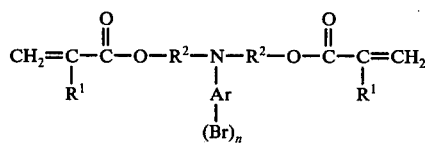

where $n$ is an integer from 1 to 6, $R^1$ is hydrogen or alkyl of 1 to 6 carbon atoms, $R^2$ is alkylene of 1 to 5 carbon atoms or

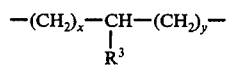

where $R^3$ is hydrogen, alkyl of 1 to 4 carbon atoms or —OH and $x$ and $y$ are selected from 0 or an integer from 1 to 4 and Ar is an aromatic group; and a reactive diluent selected from the group consisting of monoacrylates, diacrylates and triacrylates.

2. A composition according to claim 1 in which Ar is phenyl.

3. A composition according to claim 1 in which $R^1$ is alkyl, $R^2$ is

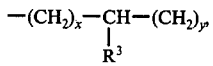

where $R^3$ is OH.

4. A composition according to claim 3 in which $R^1$ is methyl, $x$ is 1, $y$ is 1 and $n$ is 3.

5. A composition according to claim 1 in which the reactive diluent comprises dibromopropyl methacrylate.

6. A composition according to claim 1 further including from 0.1 to 1.0 percent by weight of peroxide catalyst and 0.1 to 1.0 percent by weight of accelerator.

7. A composition according to claim 1 further including from 1% to 5% by weight of an ultraviolet sensitizer.

8. A composition according to claim 1 in which the reactive diluent comprises from 5% to 20% by weight of methyl methacrylate.

9. A composition according to claim 8 in which the reactive diluent further includes an adduct of two moles of methacrylic acid and the diglycidyl ether of Bisphenol A.

10. A composition according to claim 9 in which the reactive diluent further includes a fluorinated diacrylate of the formula:

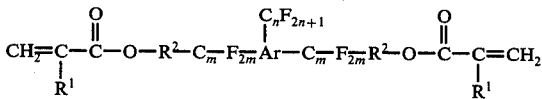

where $n$ is an integer from 1 to 8, $m$ is 0 or an integer from 1 to 5, $R^1$ is hydrogen or alkyl of 1 to 4 carbon atoms, $R^2$ is alkylene of 1 to 5 carbon atoms,

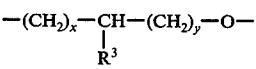

where $R^3$ is hydrogen, alkyl of 1 to 4 carbon atoms or —OH and $x$ and $y$ are selected from 0 or an integer from 1 to 5 and Ar is an aromatic group.

* * * * *